US010557797B2

(12) United States Patent
Agrawal et al.

(10) Patent No.: US 10,557,797 B2
(45) Date of Patent: Feb. 11, 2020

(54) METHOD TO DETECT BERYLLIUM BY OPTICAL FLUORESCENCE

(71) Applicant: AJJER L.L.C., Tucson, CA (US)

(72) Inventors: Anoop Agrawal, Tucson, AZ (US); Lori Adams, Tucson, AZ (US); John P. Cronin, Tucson, AZ (US)

(73) Assignee: AJJER L.L.C., Tucson, AZ (US)

( * ) Notice: Subject to any disclaimer, the term of this patent is extended or adjusted under 35 U.S.C. 154(b) by 86 days.

(21) Appl. No.: 15/571,423

(22) PCT Filed: May 26, 2016

(86) PCT No.: PCT/US2016/034339
§ 371 (c)(1),
(2) Date: Nov. 2, 2017

(87) PCT Pub. No.: WO2016/196199
PCT Pub. Date: Dec. 8, 2016

(65) Prior Publication Data
US 2018/0128743 A1 May 10, 2018

Related U.S. Application Data

(60) Provisional application No. 62/168,741, filed on May 30, 2015.

(51) Int. Cl.
G01N 21/64 (2006.01)
G01N 33/18 (2006.01)
G01N 33/24 (2006.01)
G01N 33/20 (2019.01)

(52) U.S. Cl.
CPC ......... G01N 21/6428 (2013.01); G01N 33/18 (2013.01); G01N 33/24 (2013.01); G01N 21/643 (2013.01); G01N 33/20 (2013.01); Y10T 436/255 (2015.01)

(58) Field of Classification Search
CPC ............. G01N 21/6428; G01N 21/643; G01N 21/6486; G01N 33/18; G01N 33/20; G01N 33/24; G01N 33/48; G01N 33/487; Y10T 436/19; Y10T 436/193333; Y10T 436/25375; Y10T 436/255
USPC ....... 436/63, 73, 74, 79, 124, 125, 164, 172, 436/177, 178; 422/82.08
See application file for complete search history.

(56) References Cited

U.S. PATENT DOCUMENTS

| 7,129,093 | B2 | 10/2006 | McCleskey et al. |
| 8,003,394 | B2 | 8/2011 | Agrawal et al. |
| 8,450,117 | B2 | 5/2013 | Agrawal et al. |
| 8,945,931 | B2 | 2/2015 | Agrawal et al. |
| 9,217,711 | B2 | 12/2015 | Agrawal et al. |
| 2005/0221498 | A1* | 10/2005 | McCleskey .......... G01N 21/643 436/73 |
| 2005/0280816 | A1* | 12/2005 | Agrawal .............. G01N 21/643 356/317 |
| 2010/0003760 | A1* | 1/2010 | Agrawal .............. G01N 21/643 436/27 |
| 2011/0092377 | A1 | 4/2011 | Agrawal et al. |

OTHER PUBLICATIONS

Cronin et al. J. Environmental Monitoring, vol. 10, 2008, pp. 955-960.*
Ashley et al. Analytical Methods, vol. 3, 2011, pp. 1906-1909.*
Abraham, et al 2014—Quantification and micron-scale imaging of spatial distribution of trace beryllium . . . , Journal of Microscopy (2014) doi: 10.1111/jmi.12170.
Agrawal, et al 2008—Extraction and Optical Fluorescence Method for the Measurement of . . . , Journal of Environmental Science & Technology (2008), vol. 42(6): p. 2066-2071.
Agrawal et al 2006, Validation of a Portable Fluorescence Method for the Measurement of Beryllium . . . , Journal of Environmental Monitoring (2006) vol. 8: p. 619-624.
Agrawal et al 2011 (2), Beryllium Measurement by Optical Fluorescence in Samples . . . , Journal of ASTM International (2011), vol. 8, Issue 8,DOI: 10.1520/JAI103411.
Agrawal et al 2011 Analysis of beryllium by optical fluorescence: method adaptation for manual and high throughput . . . , Proceedings WM Symposia (2011), paper 11467, Phoenix.
Ashley et al 2007—Ultra-trace determination of beryllium in occupational hygiene samples by ammonium bifluoride extraction . . . , Anal. Chim. Acta (2007), vol. 584: p. 281-286.
ASTM Test Method D7035 (2010)—Standard Test Method for Determination of Metals and Metalloids in Airborne Particulate Matter by Inductively . . . (2010), Am. Soc. Testing Mal.
ASTM Test Method D7202 (2014), Standard Test Method for Determination of Beryllium in the Workplace Using Field-Based Extraction and . . . , Am. Soc. Testing Mat.
ASTM Test Method D7458 (2014), Standard Test Method for Determination of Beryllium in Soil, Rock, Sediment, and Fly Ash Using Ammonium Bifluoride . . . , Am Soc. Testing Mat.
Goldcamp et al 2009—Extraction of Beryllium from Refractory Beryllium Oxide with Dilute Ammonium . . . ,Journal of Occupational and Environmental Hygiene, vol. 6:12, p. 735-744.
Matsumiya et al 2001—A novel fluorescence reagent, 10-hydroxybenzo[h]quinoline-7-sulfonate, for selective determination of . . . Analyst (2001),vol. 126, pp. 2082-2086.

(Continued)

Primary Examiner — Maureen Wallenhorst

(57) ABSTRACT

A method of determining beryllium or a beryllium compound thereof in a sample is disclosed by measuring fluorescence. This method discloses use of highly alkaline fluorescent indicating dye solutions with pH greater than 12.9. In a preferred embodiment the fluorescent indicating dye solutions do not contain a pH buffer. Further, the method also discloses measuring fluorescence under highly alkaline conditions, where the pH after mixing the highly alkaline fluorescent indicating dye solutions with the sample solution containing beryllium is at least 11, preferably 12. The use of highly alkaline solution provides superior detection limits for beryllium by using dilution ratios of 4× and lower.

11 Claims, 4 Drawing Sheets

(56) References Cited

OTHER PUBLICATIONS

Minogue et.al 2005—Development of a new fluorescence method for the detection of beryllium on surfaces. J. ASTM Int. (2005), vol. 2(9), 10pp. Paper ID JA113161.
NIOSH 7704—NIOSH Analytical Method, Beryllium in Air by Field-Portable Fluorometry, Method 7704, National Institute of Occupational Safety and Health, Apr. 6, 2007.
NIOSH 9110—NIOSH Analytical Method, Beryllium in Surface Wipes by Field-Portable Fluorometry, Method 9110, National Institute of Occupational Safety and Health, Apr. 6, 2007.
Straumanis et al 1955—The Rate and Mechanism of Dissolution of Purest Aluminum in Hydrofluoric Acid, vol. 102, No. 7, Journal of the Electrochemical Society (1955), p. 382-386.

* cited by examiner

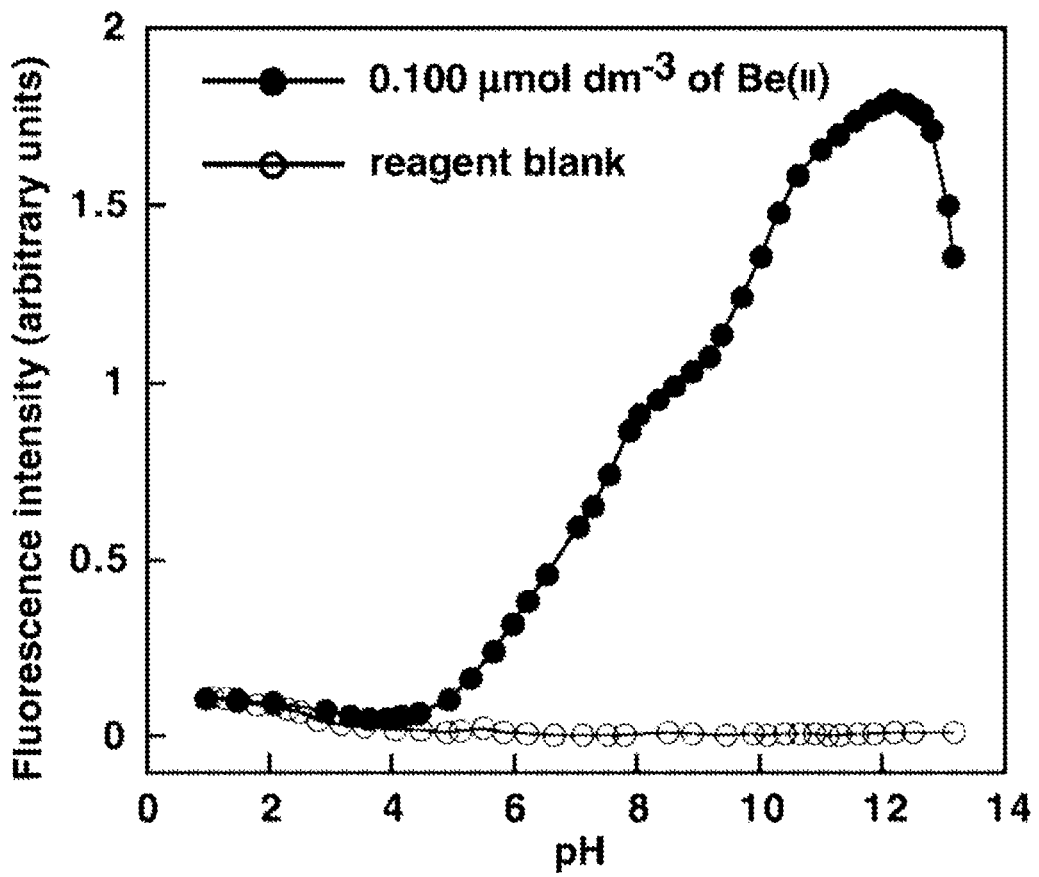
Figure 1 (prior Art, Matsumiya et al 2001)
Effects of pH on the fluorescence intensity of the Be(II)–HBQS system at $\lambda_{ex}$ = 384 nm and $\lambda_{em}$ = 478 nm. $[HBQS]_T$ = 50.9 mmol dm$^{-3}$. $[Be]_T$ = 0.100 mmol dm$^{-3}$.

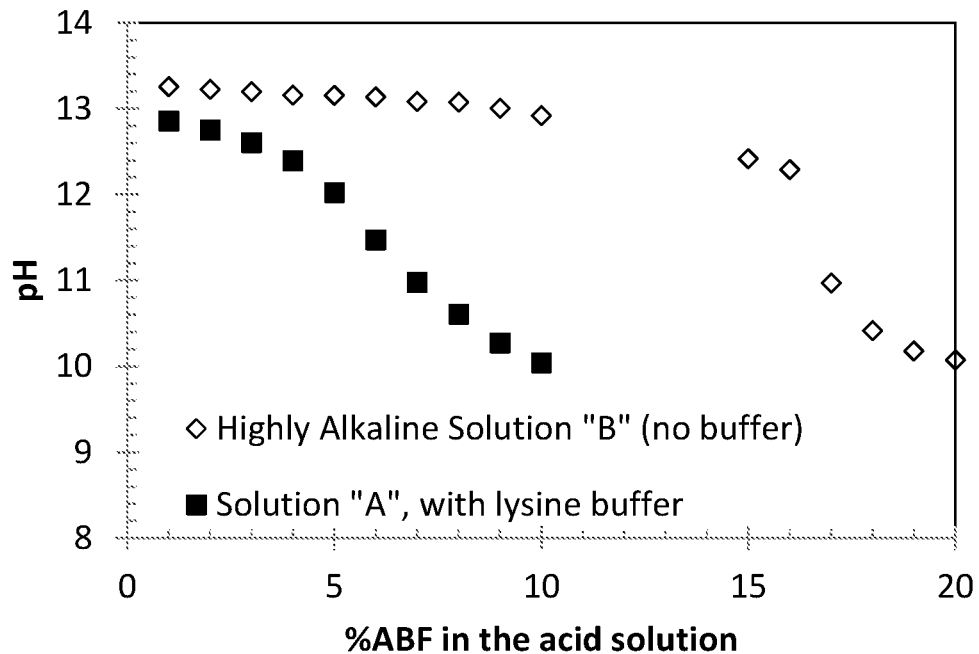
Figure 2: Effect of ABF solution concentration on pH when mixed with the dye solution in a ratio of 1:19 (no beryllium)
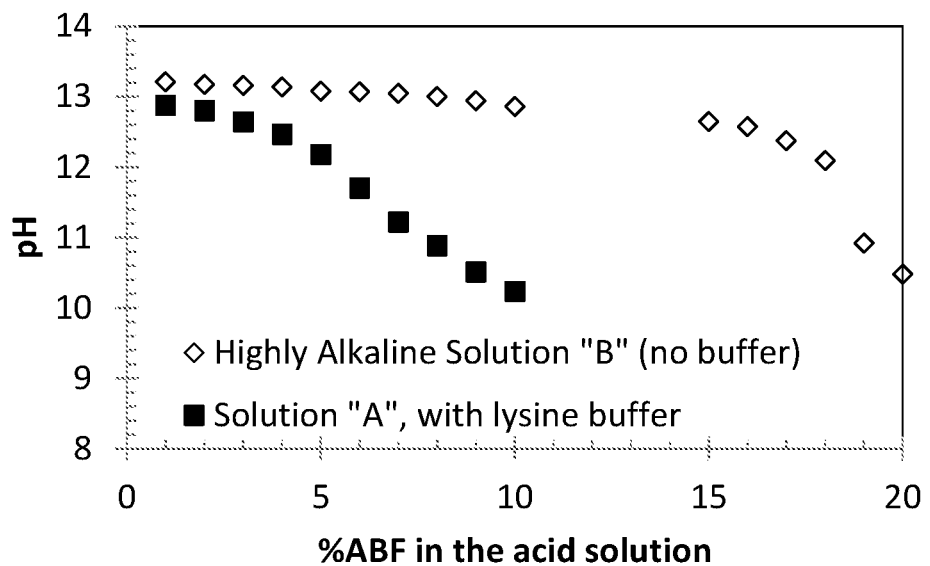
Figure 3: Effect of ABF solution concentration on pH when mixed with the dye solution in a ratio of 1:19 (4ppb Beryllium)

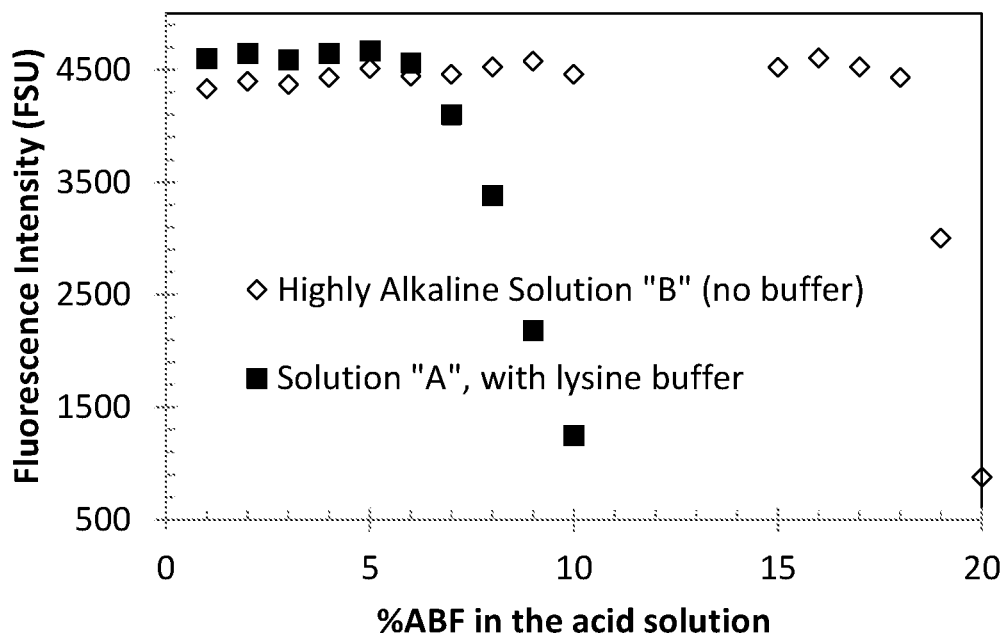
Figure 4: Effect of ABF solution concentration on fluorescent intensity when mixed with the dye solution in a ratio of 1:19 (4ppb Beryllium)
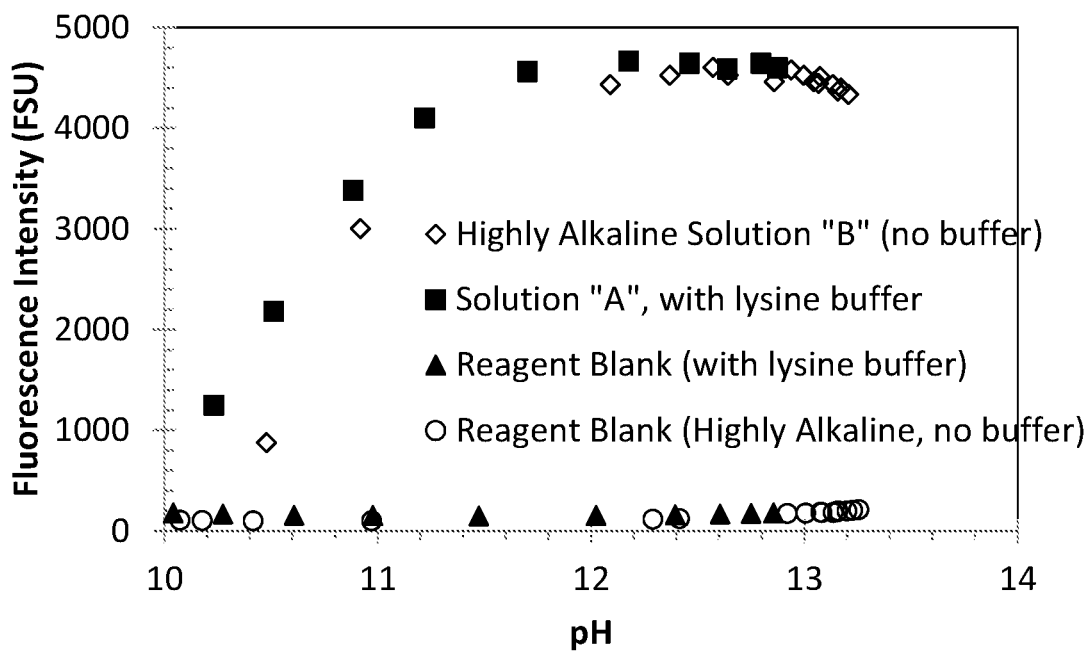
Figure 5: Effect of pH on fluorescent intensity when mixed with the dye solution in a ratio of 1:19 (with 4ppb beryllium and without beryllium)

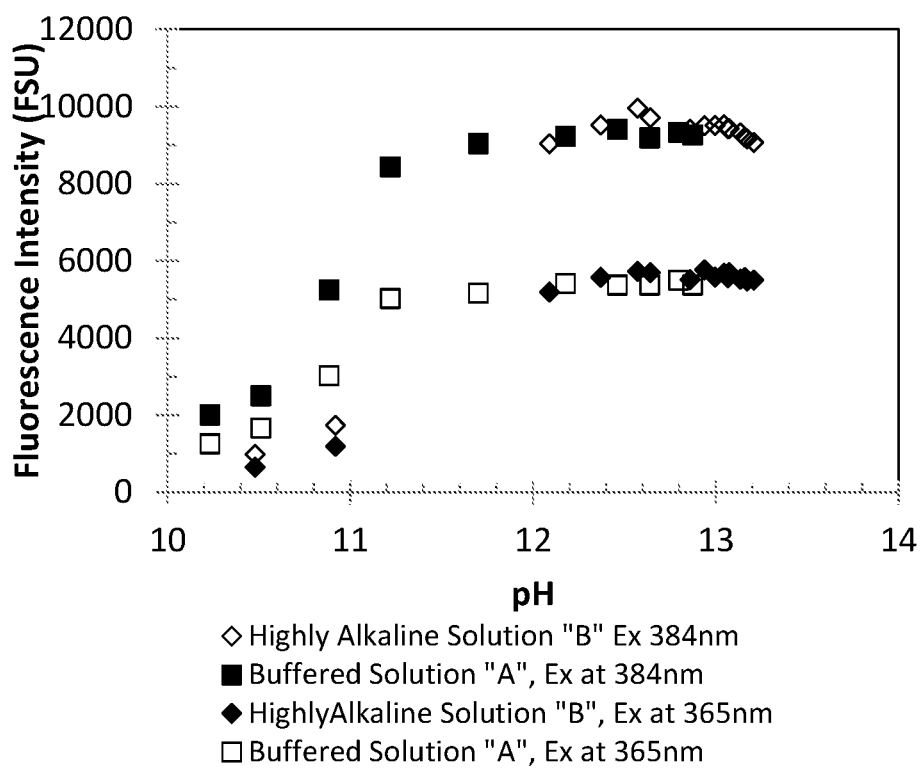
Figure 6: Effect of pH on fluorescent intensity when mixed with the dye solution in a ratio of 1:19 (with 4ppb beryllium when excited at 365nm and at 384nm, emission at 480nm)

METHOD TO DETECT BERYLLIUM BY OPTICAL FLUORESCENCE

RELATED APPLICATION/CLAIM OF PRIORITY

This application claims priority to U.S. provisional application Ser. No. 62/168,741 filed on May 30, 2015. The contents of the foregoing application are incorporated herein by reference entirely.

FIELD OF THE INVENTION

The present invention relates to the detection and quantification of beryllium by optical fluorescence. More particularly, the present invention relates to extraction of beryllium from a sample in a liquid medium or starting with a liquid sample comprising of dissolved beryllium, where such liquids are mixed with a dye solution and the dye binds with beryllium resulting in optical fluorescence. The intensity of the optical fluorescence is proportional to the amount of beryllium present in the sample. The improvement lies in making dye solutions with high alkalinity.

BACKGROUND OF THE INVENTION

Beryllium is a metal that is used in a wide variety of industries including electronics, aerospace, defense, and the Department of Energy (DOE) complexes. Exposure to beryllium containing particles can lead to a lung disease called Chronic Beryllium Disease (CBD). CBD involves an uncontrolled immune response in the lungs that can lead to deterioration in breathing capacity and ultimately death. It is clear that even in processes where beryllium dust has been controlled to very low levels, cases of disease still persist. In fact, there have been cases of CBD reported in people that have had no obvious direct contact with beryllium operations. Despite the fact that very low exposure levels can lead to CBD, the onset of disease can take decades.

Recent new regulations from DOE dictate a permissible exposure limit of 0.2 $\mu g/m^3$ in air, a housekeeping level of 3 $\mu g/100$ $cm^2$ on a surface, and a release level for materials after beryllium exposure where the surface contamination due to beryllium must not exceed 0.2 $\mu g/100$ $cm^2$. The present technique for detecting beryllium is a surface analysis that involves wiping an area with a filter paper, performing a microwave digestion with acid to dissolute beryllium or its compounds, and then analyze by inductively coupled plasma (ICP) atomic emission spectroscopy (AES). For analyzing airborne samples, one draws a known quantity of air through a filtering medium and then it is treated in a similar fashion to the surface wipes. There is a discussion in the beryllium community if the permissible air exposure limit needs to be lowered to 0.02 $\mu g/m^3$. For air sampling one cubic meter of air through the filters is typically passed in eight hours, there are also forthcoming regulations where the filters would be analyzed over shorter periods (short term exposure limits or STEL) such as 15 minutes to ensure that the rate 0.2 $\mu g/m^3$ is not exceeded in any 15 minute interval during the eight hour period, this would require one to measure beryllium after only 15 minutes of exposure and down to 0.0008 $\mu g$ on these filters. Currently, thousands of surface wipes and air filters are analyzed annually for beryllium. Similarly OSHA has been contemplating reducing air exposure limit from 2 $\mu g/m^3$ to a much lower value. In addition OSHA has detected airborne levels of beryllium at numerous sites within the United States. The ICP-AES technique requires highly trained operators and the entire sample is consumed in order to meet the detection levels so that a sample that is identified as positive for beryllium cannot be checked or verified with a second run. Optical fluorescence methods such as ASTM D7202 and ASTM D7854 and other equivalent methods (e.g., NIOSH analytical methods 7704 and 9110) remove these drawbacks and may be automated to increase throughput and decrease labor requirements. The standard fluorescence methods being currently used may be easily changed for use with present invention.

There are several publications of being able to quantitatively detect beryllium with a fluorescent indicator (Matsumiya et al 2001 or Matsumiya, Minogue et al 2005, Agrawal et al 2006, Ashley et al 2007, Agrawal et al 2008 and Agrawal et al 2011, and U.S. Pat. Nos. 7,129,093; 8,450,117; 8,945,931, and published patent application US 20110092377). All of these publications and their teachings are incorporated herein by reference.

Matsumiya teaches the use of a fluorescent dye, 10-hydroxybenzo[h]quinoline-7-sulfonate (HBQS). The HBQS dye selectively binds to beryllium and results in high fluorescence intensity at high pH. FIG. 1 has been reproduced from Matsumiya where the fluorescence intensity is shown as a function of pH when an excitation wavelength of 384 nm was used and the emission was measured at 478 nm. This clearly shows a strong dependence on pH where the maximum intensity is in the region of about 12, and a preferred range of measurement is 12 to about 12.85 with a sharp drop off after that. Thus in order to be able to detect low values of beryllium in samples by this method, an effort was made (see U.S. Pat. No. 7,129,093) to improve the dye solutions so that when sample solutions (typically acidic solutions) are mixed with dye solutions one obtains a pH in this range without having to rely on titrating back to a pH of 12 as done by Matsumiya. Another advantage of high pH of this mixture is that this solution is not able to support solubility of most metals in solution at these pH's, which precipitate out and reduce chances of interference that could have been caused by their presence. U.S. Pat. No. 7,129,093 modified Matsumiya's dye solution by adding a pH buffer (or buffer) so that when the dye solution was mixed with the acidic solution containing beryllium in a ratio of 19:1 (called 20× dilution), then the pH was maintained in the range of about 12 to 12.85 without having to titrate this mixture. Dilution ratio of 20× implies that the sample (or beryllium containing) solution has been diluted 20 times by adding the dye solution in the above volumetric ratio; similarly a dilution ratio of 5× will imply that the sample (or beryllium containing) solution has been diluted 5 times by adding the dye solution—i.e., one part by volume of the sample solution is mixed with 4 parts of the dye solution by volume and so on for other dilution ratios. However, it was important to start with a pH of about 12.85 of the buffered dye solution so that when it was mixed with the acidic samples in a dilution ratio of 20× one obtained the pH of the mixture in the range of about 12 to 12.85. This allowed simplifying Matsumiya's method since no titration was needed to maintain the pH of this mixture as long as it was in the desired pH range. In addition one did not have to worry about accounting for dilution effects caused by titration due to adding of differential volumes of the base to the solution being analyzed to bring the pH in the desired range.

U.S. Pat. Nos. 8,450,117 and 8,945,931, furthered the system where principally the dye solution described in U.S. Pat. No. 7,129,093 was used, but enhanced the sample preparation by teaching superior methods of dissolving refractory compounds of beryllium (such as high fired beryllium oxide), and increasing the method sensitivity by changing the dilution ratio to as low as 5×. Published patent application US 20110092377, adopted these methods so that all of the processing of samples-producing mixed solutions, filtering and measuring them in well plates, etc. could be automated.

The references, Minogue et al 2005, Agrawal et al 2006, Ashley et al 2007, Agrawal et al 2008 and Agrawal et al 2011, verified the system developed in the above patents and applications by providing experimental evidence of practically using the method on surface wipes, air samples, soils and other bulk samples and reaching the desired detection limits.

The present invention is a technological change over both Matsumiya and U.S. Pat. No. 7,129,093. In the current invention a highly alkaline dye solutions is used as compared to both Matsumiya and U.S. Pat. No. 7,129,093. This change in the dye solution does not impact the procedures for sample preparation including the sample dissolution methods for refractory materials or automation disclosed in the other patents and patent applications discussed above.

All of the above methods (use of titration or use of buffered solutions) were based on an observation by Matsumiya that in order to determine beryllium quantitatively using fluorescence one has to be in a pH range of about 10 to about 12.85 (with a peak intensity at about 12.6 pH), and preferably between about 11 and 12.85. Since the measurement solutions comprised of a basic dye solution and a sample solution containing beryllium which was typically acidic for most situations, the dye solution started out with a pH of 12.6 to 12.85 and when mixed with the sample solution resulted in a desired pH to make the measurements. We made a surprising discovery, that one can quantitatively determine beryllium in a wide pH range and a suitable pH can be highly basic as compared to the prior art. One can start out with dye solutions with pH at or higher than 12.9 and even make measurements at pH higher than 12.9 (i.e., after mixing with the acidic solutions) with no loss in system performance or loss in the limit of detection of the beryllium amount, and as shown even getting better detection limits when one starts out with highly alkaline solutions.

The current invention of using highly alkaline solutions overcomes several disadvantages in the prior art methods, specifically, Matsumiya's method and the method taught in U.S. Pat. No. 7,129,093 and the U.S. Pat. No. 8,945,931. The prior art methods force the preparation of solutions so that the measurement solution pH (mixture of the sample and the dye solution) is in a narrow range. In addition, use of lysine as buffer in U.S. Pat. No. 7,129,093 is not convenient. Lysine is derived from natural sources, and has different impurities depending on the source and has to be purified to get consistent fluorescence background signal. Further many of the refractory materials or particles with larger sizes of refractory materials such as high fired beryllium oxide (e.g., see Goldcamp et al 2009), beryllium ores such as beryl and bertrandite, etc., require more acidic solutions to dissolve beryllium in a reasonable time (even if elevated temperatures are used, e.g., at or below 100 C or above 100 C in pressurized vessels). These concentrated acidic solutions when mixed with buffered solutions of U.S. Pat. No. 7,129,093 will result in a large pH drop which would then decrease the fluorescent signal. One could mix the concentrated acidic solutions with water or dilute acidic solutions after beryllium has been extracted before mixing them with the dye solution, however, this decreases the amount of beryllium in the sample solution and hence compromises the system detection limit. Even further, when metal alloys such as aluminum (or its alloys) need to be dissolved in acids to determine beryllium content, one tends to use stronger acids (e.g., use of HF rather than ammonium bifluoride (ABF) solutions), then it is difficult to maintain the pH of the mixture while also maintaining high sensitivity (or lower beryllium detection limit). U.S. Pat. No. 8,945,931 makes use of the dye solutions in U.S. Pat. No. 7,129,093 but lowers the dilution ratio from 20× down to 5× to increase the detection limit. In addition, a further increase in pH of the dye solution also causes other metals to precipitate faster (e.g. iron, titanium, etc.), and reduces their interference with beryllium measurement. These metals cause the solution color to be yellow which interferes with beryllium measurement. The fluorescent method typically measure beryllium in a wide dynamic range from about 20 µg down to the limit of quantification (limit of quantification (LOQ) is typically 3.33 times the limit of detection (LOD)).

This invention uses highly alkaline dye solutions to overcome the above disadvantages.

One objective of this invention is to use highly alkaline dye solutions (which may be either buffered or non-buffered), where these are mixed with the sample solutions containing beryllium so that beryllium can be quantitatively determined using fluorescence intensity which results from the interaction between the dye and beryllium and is proportional to the beryllium content.

Another objective is to be able to use higher acidity solutions to extract beryllium from more refractory solids which can then be used to mix with dye solutions so that beryllium can be quantitatively determined using fluorescence while also allowing one to maintain finer beryllium detection limits.

Yet another objective of this invention is to substitute the buffered dye solutions in standard test methods using optical fluorescence to detect beryllium such as ASTM D7202 and ASTM D7854 and other equivalent methods where the buffered dye solution with lower pH may be substituted by the higher pH dye solutions of this invention while keeping all of the advantages of these test methods and the present innovation.

In another objective, this invention provides a procedure to be able to use dilution ratios lower than 5× to increase the system sensitivity or detect smaller amounts of beryllium.

SUMMARY OF THE INVENTION

Beryllium may be collected by wiping a surface suspected of being covered with beryllium particles (or of beryllium compounds such as beryllium oxide, beryllium containing alloys, etc.) and analyzing the wipe or by capturing particles on a filter as the air is passed through it. In both cases the wipe or the filter is first treated in the dissolution solution to extract beryllium. The method is also useful for analyzing bulk samples for the amount of beryllium such as in soils, rocks, sediments, fly ash, metals and alloys, ores, biological samples (e.g., body tissues, bones, plants, seeds) etc. Beryllium may also be quantified in already dissolved in fluids such as in water, body fluids (e.g., blood, urine and others).

The present invention provides a method of determining the presence and amount of beryllium or a beryllium compound in a sample. This includes admixing an aqueous solution containing beryllium with a highly alkaline solution containing a fluorescent indicator capable of binding beryllium to the fluorescent indicator, and, determining the presence of an amount of beryllium in the aqueous solution. Beryllium or beryllium compounds in solid samples may be extracted into an aqueous liquid solution by dissolving beryllium, and for most solid samples this extraction is carried out in acidic mediums.

BRIEF DESCRIPTION OF THE DRAWINGS

FIG. 1 Effect of fluorescence as a function of pH from a dye solution (Prior art)

FIG. 2 Fluorescence from the dye solution mixed with various concentrations of ABF solution in the mixture (reagent blank);

FIG. 3 Dependence of pH on concentration of ABF solution mixed with the dye solution with beryllium;

FIG. 4 Dependence of fluorescence on the concentration of ABF solution with beryllium;

FIG. 5 Dependence of fluorescence on pH from the dye solution mixed with ABF solution containing beryllium;

FIG. 6 Dependence of fluorescence on excitation wavelength and pH from a mixture of dye solution mixed with various concentrations of ABF solutions.

DETAILED DESCRIPTION

We made a surprising discovery that using HBQS dye solution, the drop-off in the fluorescence signal with increasing pH (above pH of 12.6 to 12.85) was not as dramatic as that reported by Matsumiya (see FIG. 1 which is reproduced from Matsumiya). This discovery opened doors for changes to this method of beryllium detection as explained below. This discovery removed the difficulties associated with U.S. Pat. No. 7,129,093 discussed above and allowed dye solutions to be made without any buffers, and making them even with pH higher than 12.85, i.e., opening a wider pH range on the higher side for carrying out these measurements. More base could be added to the dye solutions to make them even more alkaline (highly basic) so that the dye solutions could be mixed with stronger acid containing sample solutions in order to allow beryllium to be measured in the mixed or measurement solutions (mixture of dye and the sample solutions). As one measure of the high alkalinity of the dye solution, its pH should be above 12.9 and more preferably at or above 13 and most preferably at or greater than 13.1. Also the use of highly basic dye solution allows them to be mixed with stronger acidic solutions and still retain a high pH in the measurement solution. As another measure of high alkalinity of the dye solution is a test conducted by mixing this with an acidic solution—for example, when 19 parts of the highly basic dye solution of this invention is mixed with 1 part of ABF solution (dilution ratio of 20×) where the concentration of ABF solution is 7% by weight in water, then the pH of the mixture should be at or above 11 and preferably above 12. More preferably the ABF concentration in the solution should be 8% by weight and most preferably 10% by weight and still show a pH of 11 or preferably 12 or above at a dilution ratio of 20×. Some of the preferred acidic solutions and acids are ammonium bifluoride solutions, hydrofluoric acid, nitric acid, hydrochloric acid and mixtures of these. After mixing the dye solution of this invention and the beryllium containing sample solution, the pH which will result in quantitative estimation of beryllium should be above 11 and preferably above 12. These mixed solutions containing both the dye solution and the acidic sample solution may also have pH exceeding 13.

Another way to characterize the highly alkaline dye solutions with buffer is that these buffered solutions contain at least 8% more base as compared to the standard buffered dye solutions, and preferably at least 20% more. This percentage difference may be by weight of the base or by moles of the base between the said solutions. A standard buffered solution is described in U.S. Pat. No. 7,129,093 or equivalent which has been used in several of the current ASTM and NIOSH standardized test methods which use optical fluorescence to test for beryllium, as listed in the section entitled "Background of Invention". U.S. Pat. No. 7,129,093 describes making dye solutions which have a pH of 12.6, whereas the standard methods use dye solutions which have a pH of 12.85, thus for the definition of standard buffer solution (also called standard dye solution or standard buffered dye solution) and its pH for the purposes of this disclosure, the dye solutions described in the standard test methods with a pH of 12.85 is used. As an example, each liter of the standard dye solution has a nominal 2.5 N NaOH content of 82.7 ml (or 8.27%), thus for highly alkaline solutions one would use 8% or preferably 20% more NaOH which will amount to 89.3 and 99.2 ml of 2.5 N NaOH respectively.

The improved method can be used easily using the sample preparation methods taught in U.S. Pat. Nos. 8,450,117; 8,945,931 and 9,217,711. These publications teach sample dissolution at elevated temperature, use of dilution ratios lower than 20× to increase sensitivity (or detect lower amounts of beryllium). High throughput and automated sample preparation as taught in published US patent application 20110092377, and use of additives in sample solution to remove fluorescent impurities in U.S. Pat. No. 8,003,394 may also be used with the current innovation. All of these documents are included herein by reference.

Using the standard dilution ratios of 20× and 5× one can use highly alkaline solutions at pH in excess of 12.9 to obtain the same level of detection limits as buffered solutions from the prior art which use standard test methods where the pH is controlled to a lower value in a narrower range. Since the dye solutions of the present invention are more alkaline, one may use dilution ratios lower than 5× to determine beryllium in samples having very low amounts of beryllium (e.g., at or lower than 0.0002 µg in solid samples (such as wipes and air filters). For example, these may be extracted using 5 ml of acidic solutions and then mixed in dilution ratios of lower than 5× (e.g., 4× or lower) to determine beryllium content. Another advantage of using the lower dilution ratios is that one may use larger wipes or filters and extract them in a higher quantity of dissolution solution (e.g., use 10 ml or more rather than 5 ml used in several standard procedures). Since more of the dissolution solution is mixed with the dye solution when lower dilution ratios are used, one can compensate the loss of detection limit of beryllium caused by the increased volume of dissolution solution during the extraction process. In the highly alkaline solutions the fluorescent dye concentration is preferably in the range of about 30 to 120 µM although a highly preferred range is about 60 to 70 µM.

Example 1: Effect of pH on Fluorescence

The dye which was used in all of the examples was made using the procedure described in U.S. Pat. No. 7,129,093.

A standard buffered dye solution (Solution A) was made following the procedure outlined in used in standard test methods from ASTM and NIOSH listed earlier. 19.508 g of lysine (used as pH buffer), 2.208 g of ethylene diamine tetraacid disodium salt dehydrate (EDTA), 0.0382 g of HBQS dye was added to 1800 ml of DI water. Lysine was purified prior to its use. This mixture was stirred at room temperature until all components had dissolved. The pH of this solution was 4.652. To this was added 150 ml of 2.5 N of sodium hydroxide solution and the pH of the solution was 12.772, additional 17 ml of 2.5 N sodium hydroxide was added in steps to bring the pH to 12.862, finally to this 33 ml of DI water was added in steps to bring the pH to 12.856. The solution was then filtered through a nylon filter with 0.2 micron openings. The amount of 2.5 N sodium hydroxide was about 8.27% in the total dye solution.

A highly basic (i.e., highly alkaline) solution without a pH buffer (Solution B) was prepared as follows, 1.104 g of EDTA, 0.019 g of HBQS dye and 900 ml of DI water were stirred at room temperature until a clear yellow solution was obtained. To this 114.5 ml of 2.5 N NaOH was added. After mixing a clear yellow solution was obtained, this had a pH of 13.17. The solution was then filtered through a nylon filter with 0.2 micron openings. The amount of 2.5 N sodium hydroxide in the dye solution was 11.29%, i.e., the base in Solution "B" was about 36% more as compared to Solution "A" in terms of weight and also moles since in both cases sodium hydroxide of similar concentration was used. The concentration of the dye in Solution A and Solution B was the same at 61 µM. It must be noted that all of the other examples, this high alkalinity solution has been used to demonstrate the utility of this invention. However, one may use dye solutions which are more alkaline or less alkaline as long as one is within the bounds of the claims.

The pH measurements were conducted using Orion 290A+ meter and Orion probes (Thermo Electron Corporation, Beverly, Mass.) which was calibrated using buffered pH standards of 7, 10 and 13. The pH standards of 7 and 10 were obtained from ACROS (NJ) and the standard for pH 13 was obtained from Ricca Chemical Company (Arlington, Tex.). The Orion probes are Orion Ross Sure-Flow Glass combination pH electrode (part number 8172BNWP). ACROS and Thermo Electron Corporation are now part of Thermo Fisher Scientific, Pittsburgh, Pa.

Various ABF solutions were made in DI water with ABF content ranging from 1 wt % to 20 wt %. In first experiment these ABF solutions were added to the two dye solutions prepared above in a volumetric ratio of 1:19 (20× dilution, i.e., ABF solution diluted by the dye solution by 20 times) and their pH was measured. Please note there was no beryllium in these solution mixtures. Background fluorescence signal (reagent blank) was measured using Modulus spectrometer (Turner Biosystems, Sunnyvale, Calif.), which used excitation at 365 nm and emission was measured through a band pass filter with transmittance between 475 and 485 nm (or 480±5 nm). This instrument is now available under the trade name Glomax from the same manufacturer. 2 ml of liquids (measurement solution) were placed in 10 mm path length plastic cuvettes for fluorescence measurement. The results are shown in Table 1 and in FIG. 2 the effect on pH with the amount of ABF is shown. The pH of the solution mixtures (measurement solutions) made using Solution A started falling below pH 11 when these were mixed with 8% ABF solution, whereas the pH for Solution B started dropping at about 18% ABF solution. This shows that Solution B was able to tolerate more acid as compared to Solution A.

TABLE 1 pH and fluorescence intensity of reagent blank (Mixture of dye solution to acidic solution with different amounts of ABF, volumetric ratio 19:1)

| Concentration of ABF in acidic solution | Highly Basic Solution "B" (no buffer) | | Solution "A", with lysine buffer | |
|---|---|---|---|---|
| | pH | Average FSU | pH | Average FSU |
| 1% | 13.26 | 213 | 12.86 | 175 |
| 2% | 13.23 | 204 | 12.75 | 174 |
| 3% | 13.20 | 200 | 12.61 | 166 |
| 4% | 13.16 | 198 | 12.39 | 157 |
| 5% | 13.16 | 189 | 12.02 | 150 |
| 6% | 13.14 | 184 | 11.474 | 148 |
| 7% | 13.08 | 184 | 10.98 | 152 |
| 8% | 13.08 | 187 | 10.61 | 155 |
| 9% | 13.01 | 177 | 10.28 | 167 |
| 10% | 12.92 | 175 | 10.04 | 177 |
| 15% | 12.41 | 121 | | |
| 16% | 12.29 | 118 | | |
| 17% | 10.97 | 100 | | |
| 18% | 10.42 | 100 | | |
| 19% | 10.18 | 104 | | |
| 20% | 10.07 | 106 | | |

In another experiment, an 800 ppb beryllium containing liquid standard from Spex Certiprep (Metuchen, N.J.) was used as a source of beryllium to be added to the dye solution. In this liquid standard the source of beryllium is beryllium acetate. This standard containing 800 ppb of beryllium was made in 1% ABF solution. The standard solution was further diluted by mixing with a second solution using. The second solution had different amounts of ABF varying from 1 to 20% ABF solutions. One part of standard solution was diluted using 9 parts of the second solution to obtain solutions with 80 ppb beryllium in various amounts of ABF containing solutions.

1 part of the above formed solutions with 80 ppb beryllium were mixed with 19 parts of the dye solution by volume (Solution "A" or Solution "B") to obtain mixed solutions with 4 ppb of beryllium in the final mixture. These were again measured for their pH and also fluorescence as described above. These results are shown in Table 2 and in FIGS. 3 and 4. The fluorescent results have not been corrected for background (Table 1). FIG. 5 shows the dependence of fluorescent intensity on the pH (both with and without beryllium). FIG. 5 may be compared with that shown in FIG. 1 from prior art. The results from Solution "A" or "B" do not show a sharp decrease in fluorescence intensity above a pH of about 12.6, it is more clear from the presented data on Solution "B" where the pH goes to almost 13.2. Further there seems to be a rapid drop in fluorescent intensity at a pH of about 11. Also the pH drop in Solution "B" occurs around 18% ABF concentration, whereas the same happens at about 8% ABF concentration for Solution A. This shows that Solution "B" can be mixed with solutions which are more acidic and still maintain a higher pH. Further it also appears that one may increase alkalinity (i.e., increase pH) of Solution "B" further by adding more base (e.g. NaOH) and make it suitable for even more acidic solutions.

TABLE 2

Fluorescence intensity of solutions with 4 ppb of beryllium (Mixture of dye solution to acidic solution, volumetric ratio 19:1)

| ABF concentration in acidic solution | Highly Basic Solution "B" (no buffer) | | Solution "A", with lysine buffer | |
|---|---|---|---|---|
| | pH | Average FSU | pH | Average FSU |
| 1% | 13.21 | 4333 | 12.87 | 4601 |
| 2% | 13.17 | 4397 | 12.80 | 4645 |
| 3% | 13.16 | 4369 | 12.64 | 4588 |
| 4% | 13.13 | 4431 | 12.46 | 4646 |
| 5% | 13.07 | 4513 | 12.18 | 4669 |
| 6% | 13.07 | 4444 | 11.70 | 4562 |
| 7% | 13.04 | 4461 | 11.22 | 4101 |
| 8% | 13.00 | 4524 | 10.88 | 3382 |
| 9% | 12.94 | 4578 | 10.51 | 2181 |
| 10% | 12.86 | 4461 | 10.231 | 1248 |
| 15% | 12.64 | 4524 | | |
| 16% | 12.57 | 4604 | | |
| 17% | 12.37 | 4525 | | |
| 18% | 12.09 | 4432 | | |
| 19% | 10.92 | 3003 | | |
| 20% | 10.49 | 876 | | |

In addition, these results also show that the fluorescent intensity at pH 10 in Table 2 and FIG. 5 falls too low for this method to be effective to provide a reliable measurement of beryllium. Further the fluorescent intensity at pH of over 13 is almost as high as it is at about 12 and may be used for beryllium quantification. The results in Matsumiya (FIG. 1) paint a different picture where the fluorescent intensity drops at pH 13 to a level almost equivalent to pH 10. Before this discovery, in the past Matsumiya's data was considered to be a standard teaching and based on this one reached an erroneous conclusion that the high pH regime of the dye solution which may result in high pH of the measurement solution which is not suitable for beryllium quantification.

Example 2: Effect of Excitation Wavelength on Emission at Different pH

The two solutions prepared in Example 1, were analyzed by exciting them at 384 nm (using a bandpass region of 5 nm centered at 384 nm), and measuring the emission at 480 nm (in a bandpass region of 10 nm centered at 480 nm, i.e., 480±5 nm). These experiments were conducted on a RF 5301PC Spectrofluorometer from Shimadzu Scientific (Columbia, Md.). FIG. 6 shows the results on the effect of fluorescence intensity with pH. Emission results at 480 nm (in a bandpass region of 10 nm centered at 480 nm) from the same instrument are also shown when excitation wavelength of 365 nm was used (with a 5 nm bandpass centered at 365 nm). These results show that there is a higher drop in fluorescence emission at high pH when excited at 384 nm compared to the excitation at 365 nm, but it is still not as sharp as seen in FIG. 1. Further, the emission intensity at 384 nm excitation was about twice as compared to the excitation at 365 nm.

Example 3: Establishing pH with Various Dilution Ratios (for 1% and 3% ABF)

The Solutions "A" and "B" from Example 1 were mixed with 1% and 3% ABF solutions in a dilution ratio of 20× (19 parts of dye solution and 1 part of ABF solution) and 5× (4 parts of dye solution and 1 part of ABF solution). The pH of these solutions was measured as reported in Table 3. The reason for the choice of these ratios and these concentrations of ABF solutions was because dilution of 5× have been used in prior art to analyze samples to increase detection limits of wipe and air samples which are typically extracted in 1% ABF (e.g., see Agrawal et al 2006, Ashley et al 2007 and ASTM test method D 7202). 3% ABF solutions have been used to extract beryllium from bulk samples and have been typically used only in 20× dilution as at 5× dilution using standard buffered solution the pH is too low for the method to be effective. Use of highly basic solutions allows one to use 5× dilution using 3% ABF and hence allows beryllium to be detected to higher sensitivity when these solutions are used for extracting beryllium into an aqueous phase. One may even increase the alkalinity of the dye solutions further so as to use with higher concentration of ABF solutions and/or lower dilution ratios. This aspect of the innovation is further demonstrated in Example 9.

TABLE 3 pH at 20X and 5X dilutions with 1 and 3 wt % ABF when mixed with dye Solution "A" and Solution "B"

| ABF Concentration, % wt | Dilution ratio | Solution "B" | Solution "A" |
|---|---|---|---|
| 1 | 20X | 13.22 | 12.80 |
| 1 | 5X | 13.07 | 12.10 |
| 3 | 20X | 13.12 | 12.56 |
| 3 | 5X | 12.17 | 9.43 |

Example 4: Calibration Curves when the Two Dye Solutions are Mixed with Higher Proportion of Acidic Sample Solutions Calibration curves were established for both the dye solutions (Solution "A" and Solution "B"), for a dilution ratio of 5× while using 3% ABF solution and also at a dilution of 20× while using 10% ABF solution. The details of solution preparation and fluorometric evaluation using Modulus fluorometer are outlined in Example 1. The details of this calibration and the results are in Table 4.

TABLE 4

Calibration curve details

| | Type of Dye Solution | | | |
|---|---|---|---|---|
| | Highly alkaline Solution "B", no buffer | | Solution "A" buffered with lysine | |
| | ABF Concentration | | | |
| | 10% | 3% | 10% | 3% |
| | Dilution ratio | | | |
| | 20X | 5X | 20X | 5X |
| Calibration standards, ppb | 0, 1, 4, 12 and 24 | 0, 0.2, 0.8, 4 and 16 | 0, 1, 4, 12 and 24 | 0, 0.2, 0.8, 4 and 16 |
| Calibration fit, slope | 1117 | 1155 | 284 | 25.7 |
| Calibration fit, Intercept | 133 | 146 | 293 | 200 |
| Callibration fit, R² | 0.99998 | 0.99997 | 0.99624 | 0.99997 |
| pH (from Tables 2 and 3) | 12.86 | 12.17 | 10.23 | 9.43 |
| Slope ratio (Solution "B"/Solution "A") | | | 3.93 | 45 |

The results show that for the highly alkaline case, when the pH is high, the slopes are high and are virtually indistinguishable from the slopes obtained for standard analysis in Example 5, which means that the sensitivity to the change in fluorescence with changing beryllium concentration is high. This means that the detection limits for these cases will be similar to those established in Example 5.

However, for buffered Solution "A", it is clearly seen that although the linear correlation is good but the slope is extremely low. The slopes for the highly alkaline dye solution (Solution "B") to the buffered (Solution "A") are about 4 and 25 respectively for 10% ABF 20× dilution and 3% ABF solution 5×. This indicates that the limit of detection would be at least degraded by a factor of 4 and 25 for these two cases when Solution "A" is used, and is thus not suitable for a good analytical method (see next example for limit of detection analysis).

Example 5: Establishing Limit of Detection for 5× and 20× Dilution Ratios

Detection limits for beryllium were established using blanks as taught in test method ASTM D7035-10 (Standard Test Method for Determination of Metals and Metalloids in Airborne Particulate Matter by Inductively Coupled Plasma Atomic Emission Spectrometry (ICP-AES)). These detection limits were established by generating data on the Modulus spectrometer instrument and parameters described in Example 1. These were established using dye Solution "A" (with lysine buffer) and highly alkaline Solution "B" as described in Example 1, using 1% ABF solution when it was mixed with the dye solution in a dilution ratio of 5× and 20×. For each set, ten Whatman filters 541 (47 mm in diameter) obtained from Thermo Fisher were dropped in 10 different plastic vials containing 5 ml of the ABF solution. Whatman filters are used as wipes to obtain surface samples (e.g., see ASTM test method D7202). The vials were capped and heated to 90° C. for one hour, to mimic extraction of beryllium from the wipes. These were blanks as there was no added beryllium. The solutions were cooled and then these were mixed with the appropriate dye solution. The fluorescence from these was read on the fluorometer and average value and standard deviation was calculated. In addition calibration solutions were made with known amount of beryllium in 1 and 3% ABF solutions and were mixed with either dye solution A or B in 20× or in 5× dilution ratio. As an example to calculate detection limit for Solution "A" in 3% ABF solution at 20×, calibration curve was generated by combining 1.9 ml of Solution A with 0.1 ml of 3% ABF solution containing different amount of beryllium and mixed (20× dilution ratio). The results for Whatman filters are shown in Table 5. The concentration of beryllium in calibration solutions (i.e. mixture of the dye and the ABF solution) are expressed in ppb. The linear regression values which fit the various calibration curves are also given in this table. The limit of detection in ppb was calculated as 3*(Std deviation from blanks)/(Calibration fit slope)

As an example for high alkalinity solution with no buffer detection limit would be 3*4.2/1021=0.012 ppb. For conversion to µg of beryllium on the solid sample such as filter or a wipe it was assumed that the beryllium from the sample was extracted in 5 ml of ABF solution and then 0.1 ml of the sample solution was combined with 1.9 ml of the dye solution for 20× dilution and 0.4 ml of the sample solution was combined with 1.6 ml of the dye solution for 5× dilution.

TABLE 5

Establishing limit of detection for the method using Whatman filters which are typically used as surface wipes.

| | Type of Dye Solution | | | |
|---|---|---|---|---|
| | Highly alkaline Solution B, no buffer | | Solution "A" buffered with lysine | |
| | ABF Concentration | | | |
| | 1% | 1% | 1% | 1% |
| | Dilution ratio | | | |
| | 20X | 5X | 20X | 5X |
| Average Fluorescent reading from 10 blanks | 225 | 233 | 193 | 264 |
| Std. Deviation of Fluorescent reading from 10 blanks | 4.2 | 9.1 | 3.5 | 12.8 |
| Calibration standards, ppb | 0, 0.05, 0.2, 0.5, 2 | 0, 0.05, 0.1, 0.2, 0.8 | 0, 0.05, 0.2, 0.5, 2 | 0, 0.05, 0.1, 0.2, 0.8 |
| Calibration fit, slope | 1021 | 1076 | 1102 | 1141 |
| Calibration fit, Intercept | 207.0 | 169.2 | 173.8 | 146.5 |
| Calibration fit, $R^2$ | 1.0000 | 0.9997 | 0.9999 | 0.9998 |
| Detection limit, ppb beryllium | 0.0123 | 0.0255 | 0.0096 | 0.0337 |
| Detection limit, µg of beryllium | 0.0012 | 0.00064 | 0.00096 | 0.00084 |

Similarly, detection limits of the method were established using blank MCE 0.8 micron filters (MCE is mixed cellulose ester, obtained from SKC Inc., Eighty Four, Pa.). These are typically used for air sampling. The results are shown in Table 6.

TABLE 6

Establishing limit of detection for the method using MCE filters (typically used for sampling air)

| | Type of Dye Solution | | | |
|---|---|---|---|---|
| | Highly alkaline Solution B, no buffer | | Solution "A" buffered with lysine | |
| | ABF Concentration | | | |
| | 1% | 1% | 1% | 1% |
| | Dilution ratio | | | |
| | 20X | 5X | 20X | 5X |
| Average Fluorescent reading from 10 blanks | 211 | 179 | 179 | 161 |
| Std. Deviation of Fluorescent reading from 10 blanks | 2.5 | 7.5 | 2.1 | 5.7 |
| Calibration standards, ppb | 0, 0.05, 0.2, 0.5, 2 | 0, 0.05, 0.1, 0.2, 0.8 | 0, 0.05, 0.2, 0.5, 2 | 0, 0.05, 0.1, 0.2, 0.8 |
| Calibration fit, slope | 1021 | 1076 | 1102 | 1141 |
| Calibration fit, Intercept | 207.0 | 169.2 | 173.8 | 146.5 |
| Calibration fit, $R^2$ | 1.0000 | 0.9997 | 0.9999 | 0.9998 |
| Detection limit, ppb beryllium | 0.0072 | 0.021 | 0.0056 | 0.015 |
| Detection limit, µg of beryllium | 0.00072 | 0.00054 | 0.00056 | 0.00037 |

The detection limits for all of these methods are very low and is at or below 0.001 µg of beryllium or better. The limit of detection using MCE filters is superior. In terms of ppB of beryllium which can be detected in the mixture of the sample and the dye solution, 20× provides a detection which is about a factor of 2 to 3 better as compared to 5×, however, 5× still translates to a better detection limit in terms of beryllium amount on the solid sample due to lower dilution. As demonstrated in Example 9, the detection limit may be further improved by going to dilution ratios lower than 5×, as long as the pH of the mixture of the dye solution and the sample solution is at least 11, preferably at least 12. Further, as shown high alkalinity solutions are more suitable for this.

Example 6: Analysis of Wipes and Air Filters

In this experiment dye Solution "A" and dye Solution "B" were evaluated to quantify beryllium values in spiked filters used as surface wipes (Whatman 541) and also MCE air filters (the solutions and the instrument used are described in Example 1). The filters were spiked with high fired beryllium oxide and were obtained from High Purity Standards (Charleston, S.C.). Beryllium oxide used for spiking the filters was NIST (National Institute of Standards and Technology, Gaithersburg, Md.) Standard Reference Material (SRM) 1877. The stated value of beryllium on the filters is within ±10% and within ±20% for very low beryllium contents. These filters were put in closed plastic vials with 5 ml of 1% ABF solution, and heated for one hour at 85° C. to extract beryllium into the ABF solution. Each of these solutions was analyzed after cooling to room temperature and mixing them with highly alkaline Solution "B" and separately with Solution "A". This analysis was done in triplicate using dilutions of both 5× and 20× following ASTM D7202 guidelines. The calibration curve details for the four sets of evaluation are shown in Table 7. Results of evaluation using a dilution ratio of 5× are shown in Table 8 and for 20× in Table 9.

TABLE 7

Calibration curve details

| | Type of Dye Solution | | | |
|---|---|---|---|---|
| | Highly alkaline Solution B, no buffer | | Solution "A" buffered with lysine | |
| | Calibration standards, ppb | | | |
| | 0, 0.05, 0.2, 0.5, 2 | 0, 0.2, 0.8, 4 and 16 | 0, 0.05, 0.2, 0.5, 2 | 0, 0.2, 0.8, 4 and 16 |
| | ABF Concentration | | | |
| | 1% | 1% | 1% | 1% |
| | Dilution ratio | | | |
| | 20X | 5X | 20X | 5X |
| Calibration fit, slope | 1021 | 1115 | 1102 | 1141 |
| Callibration fit, Intercept | 207.0 | 163.2 | 173.8 | 146.5 |
| Callibration fit, $R^2$ | 1.0000 | 0.99999 | 0.9999 | 0.9998 |

The standard deviations in Tables 8 and 9 relate to the three measurements made by analyzing three different aliquots of a solution extracted from each filter. The average and standard deviation (number shown after "±" sign) correspond to these three readings. Further, three or four filters (A, B, C and D) of each type were analyzed. These readings are reported separately due to a variability of beryllium content amongst the filters even when they have the same nominal value.

TABLE 8

Determination of beryllium on spiked filters using 5X dilution

| Filter type | Nominal spike level of beryllium, µg (ppb) | Highly alkaline Solution "B", no buffer Analyzed value of beryllium | | Solution "A" buffered with lysine Analyzed value of beryllium | |
|---|---|---|---|---|---|
| | | µg | ppb | µg | ppb |
| A, MCE | 0.025 (1) | 0.030 ± 3.1E−05 | 1.2 ± 0.0012 | 0.034 ± 8.9E−06 | 1.36 ± 0.0004 |
| B, MCE | 0.025 (1) | 0.031 ± 1.3E−04 | 1.22 ± 0.0053 | 0.033 ± 6.7E−05 | 1.34 ± 0.0027 |
| C, MCE | 0.025 (1) | 0.031 ± 7.9E−05 | 1.22 ± 0.0032 | 0.034 ± 1.0E−04 | 1.36 ± 0.0040 |
| D, MCE | 0.025 (1) | 0.03 ± 5.7E−05 | 1.22 ± 0.0023 | 0.035 ± 1.1E−05 | 1.38 ± 0.0044 |
| A, MCE | 0.2 (8) | 0.204 ± 1.2E−04 | 8.15 ± 0.0048 | 0.210 ± 1.8E−04 | 8.39 ± 0.0072 |
| B, MCE | 0.2 (8) | 0.203 ± 1.4E−04 | 8.13 ± 0.0054 | 0.206 ± 1.8E−04 | 8.24 ± 0.0073 |
| C, MCE | 0.2 (8) | 0.207 ± 1.7E−04 | 8.29 ± 0.0069 | 0.208 ± 3.0E−04 | 8.31 ± 0.012 |
| D, MCE | 0.2 (8) | 0.205 ± 1.2E−04 | 8.20 ± 0.0047 | 0.206 ± 2.4E−04 | 8.24 ± 0.0095 |
| A, WHT | 0.005 (0.2) | 0.007 ± 2.2E−05 | 0.27 ± 0.0009 | 0.007 ± 2.5E−05 | 0.28 ± 0.0010 |
| B, WHT | 0.005 (0.2) | 0.007 ± 2.8E−05 | 0.27 ± 0.0011 | 0.007 ± 3.7E−05 | 0.28 ± 0.0015 |
| C, WHT | 0.005 (0.2) | 0.007 ± 2.3E−05 | 0.27 ± 0.0009 | 0.007 ± 3.1E−05 | 0.27 ± 0.0012 |
| A, WHT | 0.002 (0.08) | 0.004 ± 1.7E−05 | 0.15 ± 0.0010 | 0.004 ± 1.8E−05 | 0.16 ± 0.0007 |
| B, WHT | 0.002 (0.08) | 0.004 ± 2.5E−05 | 0.17 ± 0.0008 | 0.004 ± 1.3E−05 | 0.17 ± 0.0051 |
| C, WHT | 0.002 (0.08) | 0.004 ± 2.0E−05 | 0.15 ± 0.0006 | 0.004 ± 2.3E−05 | 0.15 ± 0.0009 |
| B, WHT | 0.02 (0.8) | 0.022 ± 1.8E−05 | 0.88 ± 0.0007 | 0.024 ± 8.5E−05 | 0.95 ± 0.0034 |
| C, WHT | 0.02 (0.8) | 0.022 ± 1.7E−05 | 0.89 ± 0.0007 | 0.023 ± 3.5E−05 | 0.91 ± 0.0014 |
| A, WHT | 2 (80) | 2.03 ± 1.3E−03 | 81.15 ± 0.051 | 2.00 ± 2.2E−03 | 80.06 ± 0.088 |
| B, WHT | 2 (80) | 2.01 ± 5.8E−04 | 80.50 ± 0.023 | 2.04 ± 2.9E−03 | 81.6 ± 0.116 |
| C, WHT | 2 (80) | 2.04 ± 5.2E−04 | 81.61 ± 0.021 | 2.03 ± 2.0E−03 | 81.0 ± 0.079 |

WHT represents Whatman filters

TABLE 9

Quantification of beryllium on various spiked filters using 20X dilution

| Filter type | Nominal spike level of beryllium, μg (ppb) | Highly alkaline Solution "B", no buffer Analyzed value of beryllium | | Solution "A" buffered with lysine Analyzed value of beryllium | |
|---|---|---|---|---|---|
| | | μg | ppb | μg | ppb |
| A, MCE | 0.025 (0.25) | 0.038 ± 6.7E−05 | 0.38 ± 0.0007 | 0.035 ± 1.9E−04 | 0.35 ± 0.0019 |
| B, MCE | 0.025 (0.25) | 0.037 ± 6.9E−05 | 0.37 ± 0.0007 | 0.039 ± 3.1E−04 | 0.39 ± 0.0031 |
| C, MCE | 0.025 (0.25) | 0.039 ± 5.7E−05 | 0.39 ± 0.0006 | 0.038 ± 1.2E−04 | 0.38 ± 0.0012 |
| D, MCE | 0.025 (0.25) | 0.037 ± 4.8E−05 | 0.37 ± 0.0005 | 0.037 ± 1.1E−04 | 0.37 ± 0.0011 |
| A, MCE | 0.2 (2) | 0.189 ± 1.4E−04 | 1.89 ± 0.0014 | 0.189 ± 2.0E−04 | 1.89 ± 0.0020 |
| B, MCE | 0.2 (2) | 0.190 ± 2.1E−03 | 1.90 ± 0.0206 | 0.188 ± 1.7E−04 | 1.88 ± 0.0017 |
| C, MCE | 0.2 (2) | 0.192 ± 2.0E−04 | 1.92 ± 0.0020 | 0.190 ± 2.8E−04 | 1.90 ± 0.0028 |
| D, MCE | 0.2 (2) | 0.189 ± 1.2E−04 | 1.89 ± 0.0012 | 0.191 ± 2.3E−04 | 1.91 ± 0.0023 |
| A, WHT | 2 (20) | 1.795 ± 1.3E−03 | 17.95 ± 0.0126 | 1.674 ± 5.2E−04 | 16.74 ± 0.0052 |
| B, WHT | 2 (20) | 1.805 ± 3.0E−03 | 18.05 ± 0.0030 | 1.776 ± 2.0E−03 | 17.76 ± 0.0201 |
| C, WHT | 2 (20) | 1.803 ± 3.2E−04 | 18.03 ± 0.0032 | 1.782 ± 1.5E−03 | 17.82 ± 0.0150 |
| A, WHT | 0.02 (0.2) | 0.012 ± 1.9E−05 | 0.12 ± 0.0002 | 0.011 ± 8.1E−05 | 0.11 ± 0.0008 |
| B, WHT | 0.02 (0.2) | 0.031 ± 7.1E−05 | 0.31 ± 0.0007 | 0.030 ± 4.8E−05 | 0.30 ± 0.0005 |
| C, WHT | 0.02 (0.2) | 0.030 ± 2.4E−05 | 0.30 ± 0.0002 | 0.029 ± 5.7E−05 | 0.29 ± 0.0006 |

The results on beryllium quantification on the wipes and air filters show that the two solutions are very comparable both at 5× and at 20× dilutions. The use of highly alkaline solution does not compromise the analytical capabilities of the system.

Example 7: Effect of Interference by Iron

This experiment was done to evaluate if there would be any effect of interference from other metals using highly alkaline solutions. Iron was chosen for this as it has been shown in the past that this and also to some extent titanium cause most interference by imparting a yellow color to the measurement solution (mixture of the dye solution and the sample solution). In Example 8, soils were analyzed, which typically comprise of many elemental components (see Appendix 1), and no interference was found while measuring beryllium. This yellowness interferes with fluorescence and reduces the signal, thus biasing the results towards reduced amount of beryllium. The yellowness in the solutions may be removed by immediately filtering these solutions through hydrophilic filters of pore size 0.2 μm or finer, or one can wait for two hours for these metal impurities to settle out and then filtering the solutions. The solutions were made using a solution with a known amount of beryllium (obtained from Spex Certiprep) and ferric chloride (as a source of iron) in the ABF solution (1% and in 3% by weight ABF solutions in water) and then mixed with the appropriate dye solution in the two dilution ratios 5× and 20×. In one set the solutions were immediately filtered through Acrodisc 25 mm syringe filters with a hydrophilic membrane (0.2 μm GHP membrane). The filters are made by Pall Life Sciences and available from VWR (Radnor, Pa.). Another set of solutions was left standing for two hours and then filtered using similar filters. The filtered solutions were evaluated for fluorescence on Modulus instrument as in Example 1. Control samples with the same concentration of beryllium but without iron were also measured. In each series (i.e., for a specific dye solution used, ABF concentration and the dilution ratio) the fluorescence intensity was normalized on a scale of 100 to the sample without iron within the same series and the data is shown in Table 10. In all of the solutions (mixtures of the dye and the sample solutions) beryllium concentration was 0.1 ppb. The iron concentration in solutions with 20× dilution ratio was 1.1 ppm and for 5× it was 4.4 ppm. Thus, in each case the iron concentration was more than 10,000 times the beryllium concentration.

TABLE 10

Effect of iron on interference with beryllium measurements

| Type of Dye Solution4 | Highly alkaline Solution "B", no buffer | | | | Solution "A" buffered with lysine | | | |
|---|---|---|---|---|---|---|---|---|
| ABF Concentration | 1% | | 3% | | 1% | | 3% | |
| Dilution ratio | 20X | 5X | 20X | 5X | 20X | 5X | 20X | 5X |
| Fluorescence Intensity, No iron | 100.0 | 100.0 | 100.0 | 100.0 | 100.0 | 100.0 | 100.0 | 100.0 |
| Fluorescence intensity, filtered immediately | 99.9 | 100.1 | 97.1 | 100.9 | 100.1 | 93.1 | 98.6 | 96.2 |
| Fluorescence intensity, filtered after two hours | 99.9 | 102.2 | 100.7 | 99.8 | 100.8 | 99.3 | 102.3 | 97.5 |

The results show that there is no appreciable effect of iron on fluorescence intensity when the solutions are evaluated after mixing and immediate filtration or waiting for two hours after mixing and then filtering. The latter process is slightly preferred for Solution "A", particularly when solutions with higher acid contents are used (i.e., 5× dilution), whereas for highly alkaline solutions there is no difference. Thus the impact of interference is low when either of the dye solutions is used, but the results for high acid content mixtures are superior for Solution "B", especially if one needs to carry out an analysis of filtered solutions without waiting.

Example 8: Analysis of Bulk Samples (Soils)

The various soil samples were analyzed following the experimental procedure in ASTM D7854. The soil samples, 0.5 gm of each of, were heated with 50 ml of 3% ABF solution at 90 C for 40 hours in an oven to extract beryllium into the solution. These solutions were heated in capped polypropylene vials. The samples after heating were cooled and then filtered through Acrodisc 25 mm syringe filters with a hydrophilic membrane (0.2 μm GHP membrane). The filtered solutions were mixed separately with the two dye solutions (Solution "A" and Solution "B") using a 20× dilution ratio. After mixing, the solutions were left standing for two hours and were filtered again using Acrodisc 25 mm syringe filters with a hydrophilic membrane (0.2 µm GHP membrane). When samples 2728-004 were analyzed, the beryllium reading exceeded the maximum calibration standard by almost 3 times. Thus the aliquot of the dissolution solution was diluted by adding an equal amount of 3% ABF solution, and then this solution was analyzed using a dilution ratio of 20×.

The three samples included in this analysis were, NIST Standard Reference Material 2710 (Montana soil) with a reported beryllium value of 2.5±0.07 µg and the two spiked soil samples 2728-002 and 2728-004 with a reported beryllium content of 4.36 µg±0.69 µg and 124 µg±7 µg. The latter two samples were prepared by High Purity Standards, and these were produced by spiking CCRMP Till-1 Soil (obtained from Natural Resources Canada, Ontario, Canada) with high fired beryllium oxide (beryllium oxide was NIST Standard Reference Material 1877). The natural beryllium content for CCRMP Till-1 Soil has a reference value of 2.4 ppm. Soils comprise of many elements, the certified values of various elements in these soils are compiled in Appendix A.

Two sets of calibration curves were generated using Solution "A' and another Solution "B". The details of these curves are in Table 11. The calibration curves were made using 1% ABF solution and the 800 ppm standard from Spex Certiprep as outlined in Example 1. Since these standards were made in 1% ABF and the soils were extracted in 3% ABF, a sample was made as "reference check" in 3% ABF which had 1 ppb beryllium after mixing with the dye solution. The experimental value determined from fluorescence for "reference check" is also shown in Table 11, which agrees very well with the expected value for both cases.

TABLE 11

Calibration curve details and reference check

| | Type of Dye Solution | |
|---|---|---|
| | Highly alkaline Solution "B", no buffer | Solution "A" buffered with lysine |
| Calibration standards, ppb | 0, 0.5, 2, 10, 40 | 0, 0.5, 2, 10, 40 |
| ABF Concentration | 1% | 1% |
| Dilution ratio | 20X | 20X |
| Calibration fit, slope | 1052 | 1083 |
| Calibration fit, Intercept | 204.1 | 252.1 |
| Calibration fit, $R^2$ | 0.99999 | 0.99997 |
| Reference Check sample in 3% ABF, 1 ppb beryllium (Average ± Std dev, n = 3) | 1.01 ± 0.007 | 0.96 ± 0.000 |

Each sample was extracted in the ABF and from it three different aliquots were taken and analyzed. Each aliquot along with the dye solution was taken in a cuvette and analyzed three times giving a total of 9 readings. The data on each extraction is reported separately in Table 12, and the twelve readings are reported as average±std deviation.

In another repeat experiment for Montana SRM, 50 mg of washed activated charcoal was added (Agrawal et al 2001 (2), and ASTM D7202) in the dissolution solution while the dissolution was carried out at 90 C. This was done to remove any fluorescent impurities (organic materials) which may be present in the samples. Soils may be particularly prone to be contaminated by organic materials which may give rise to increased fluorescence and may lead to overestimation of beryllium. After dissolution process in the first filtration step the charcoal is removed so that when an aliquot of sample is removed to be added to the dye solution for analysis, there is no charcoal present (See U.S. Pat. No. 8,003,394 for additional details). The rest of the analytical procedure was similar to the samples above without charcoal. All of these results are shown in Table 12.

TABLE 12

Soil analysis (µg beryllium/g of soil)

| Type of Dye Solution | Highly alkaline Solution "B", no buffer | | | | Solution "A" buffered with lysine | | | |
|---|---|---|---|---|---|---|---|---|
| Charcoal Treated? | Yes | | No | | Yes | | No | |
| Beryllium amount/g of soil | µg | Recovery % | µg | Recovery % | µg | Recovery % | µg | Recovery % |
| Montana soil, SRM2710 | 2.27 ± 0.010 | 91 | 2.89 ± 0.042 | 115.4 | 2.14 ± 0.016 | 86 | 2.81 ± 0.019 | 112.5 |
| SM-2728-002 | | | 4.60 ± 0.035 | 91 | | | 4.58 ± 0.097 | 91.0 |
| SM-2728-0024 | | | 110.3 ± 1.39 | 89 | | | 112.8 ± 0.75 | 91.0 |

Recovery numbers are based on average beryllium content for these standards

These results show that there is little difference between the use of the two dye solutions in terms of being in the range of analytical accuracy and precision. Since soils contain many different elements (see Appendix 1 for the composition of these soils), these results also show that using this method there is no interference by the other elements on beryllium value determination. However, if one needs to increase the method sensitivity by using 5× dilution then one will have to use the highly alkaline dye solution as discussed in Examples 3 and 4. One may further increase the detection limit by decreasing the dilution ratios lower than 5× (e.g., 4× or lower) by using higher alkalinity solutions, so that the pH of the measurement solutions is still above 12.

Example 9: Increase in Limit of Detection Using Higher Alkalinity Solutions and Smaller Dilution Ratios In this example, the two solutions prepared in Example 1 were evaluated by mixing them with 1% ABF solution in different dilution ratios starting from 5× and below. The results of pH and relative fluorescence (fluorescence of solutions with 0.005 ppb of beryllium and no beryllium are shown in Table 13.

TABLE 13

Relative fluorescence in solution mixtures comprising 0.005 ppb beryllium to solutions without beryllium. pH values are shown for solution mixtures containing 0.005 ppb beryllium.

| | | Type of Dye Solution | | | |
|---|---|---|---|---|---|
| | | Highly alkaline Solution B, no buffer | | Solution "A" buffered with lysine | |
| Dilution ratio | μg on filter | pH | Relative fluorescence | pH | Relative fluorescence |
| 5X | 0.000125 | 12.98 | 1.03 | 11.85 | 1.07 |
| 4X | 0.000100 | 12.91 | 1.02 | 10.99 | 1.05 |
| 3X | 0.000075 | 12.66 | 1.06 | 9.89 | 0.99 |
| 2X | 0.000050 | 9.14 | 1.03 | 8.53 | 1.01 |

It has been established before that using dilution ratio of 5× results in enhanced detection limit for beryllium for the both of the dye solutions. To quickly understand if the detection limit can be further enhanced using lower dilution ratios the data in Table 13 was generated. This shows that below 5× dilution (e.g., 4× or lower), the pH of the mixed solution using dye Solution "A" rapidly degrades and the same is not seen for high alkalinity Solution "B" when the dilution ratio is changed from 4× to 2×. Further, even with a small amount of beryllium in the solution one is able to see increased fluorescence at 3× for the high alkalinity solutions. Thus it was decided to establish beryllium detection limits at dilution ratio of 3×. The results are shown in Table 14. Blank MCE filters were used to establish this limit (as in Example 5). These filters were extracted in 1% ABF solution at 85° C. for one hour in capped plastic vials. After cooling to room temperature, 0.67 ml of this solution was added to 1.33 ml of the dye solution (Solution "A" or Solution "B") and their fluorescence measured as in Example 1 on Modulus instrument. Two sets of calibration solutions in 1% ABF with different amounts of beryllium were used to determine the detection limits. These standards were mixed with the Dye solutions "A" and "B" in a dilution ratio of 3×. As seen in Table 14, use of standards with different amounts of beryllium had no discernible impact on the results. The detection limits using 3× dilution ratio when highly alkaline solutions were used were almost four times better in ppb as compared to the results obtained from a dilution ratio of 5× (see Example 5 or Ashley et al 2007). However, for standard buffered dye solution (Solution "A") a degradation of the results is seen, as the calibration slope is much shallower. In terms of μg on filter, the results are almost an order of magnitude better for high alkaline solutions as compared to dilution ratio of 5× (see Example 5), and the results degrade for the standard buffered dye solutions.

TABLE 14

Limit of detection at dilution ratio of 3X

| | Type of Dye Solution | | | |
|---|---|---|---|---|
| | Highly alkaline, Solution "B", no buffer | | Solution "A" buffered with lysine | |
| | ABF Concentration | | | |
| | 1% | 1% | 1% | 1% |
| | Dilution ratio | | | |
| | 3X | 3X | 3X | 3X |
| | Calibration standards, ppb | | | |
| | 0, 0.2, 0.8, 4 and 16 | 0, 0.05, 0.1, 0.2 and 0.8 | 0, 0.2, 0.8, 4 and 16 | 0, 0.05, 0.1, 0.2 and 0.8 |
| Calibration fit, slope | 1193.0 | 1224.7 | 192.6 | 203.2 |
| Callibration fit, Intercept | 158.0 | 118.8 | 150.1 | 143.1 |
| Callibration fit, $R^2$ | 1.0000 | 1.0000 | 0.9999 | 0.9980 |
| Average Fluorescent reading from 10 blanks | 149.5 | | 201.2 | |
| Std. Deviation of Fluorescent reading from 10 blanks | 2.52 | | 4.52 | |
| Detection limit, ppb beryllium | 0.0063 | 0.0062 | 0.0704 | 0.0668 |
| Detection limit, μg of beryllium | 0.00010 | 0.00009 | 0.0011 | 0.0010 |

Usually one considers that the limit of quantification (LOQ) is about 3.33 times higher than the limit of detection (LOD), thus this LOQ is suitable to measure filters containing 0.0008 μg as required by STEL conditions discussed earlier.

This example shows how to further enhance the detection limit by use of high alkalinity dye solutions and using lower dilution ratios. Using the highly alkaline dye solutions, one still has to ensure that the pH of the measurement solution after adding the sample solution (which is typically acidic) should be higher than 11, preferably at or higher than 12. One can further optimize the system and increase the alkalinity of the dye solution even more so that one may use dilution ratios of 2× or even lower to get additional enhancement of sensitivity i.e., further lower the detection limits of beryllium (i.e. lower than 0.0001 μg on a solid media).

When using this invention, particularly to obtain very high sensitivity (dilution of 5× or lower, or preferably dilution of 4× or Lower), it is important that the sample not have a background fluorescence, i.e., the liquid solution such as the acidic solution after extracting beryllium from the sample does not have an elevated fluorescence from a fluorescing impurity, i.e. the fluorescence (or background fluorescence) of the sample prior to mixing with the dye solution must be low and preferably within 50% of the blank acidic solution (i.e., the acidic solution which has not been used to extract the sample as yet), and more preferably within 25% of the blank acidic solution. If the background fluorescence is high then the lower dilution ratios may not result in enhanced sensitivity and the sensitivity may even be poorer as compared to those obtained with high dilution ratios such as 20×. One way to overcome this is to use the method described in U.S. Pat. No. 8,003,394 where the acidic solution is treated with an additive. Typically this additive is cleaned charcoal which is added to the acid solution as beryllium is extracted from the sample at elevated temperature, or added to a liquid sample containing beryllium and then heated to an elevated temperature generally to 80 to 100 C for 30 minutes or more as discussed earlier for beryllium dissolution. Typical range of additive is about 0.1 to 10 mg and preferably 0.5 to 2 mg per ml of the acidic solution. After the treatment the solution is cooled and the additive is removed by filtration or other means before adding this to the dye solution. The additive combines with the fluorescing impurities (which are organic materials) and such organic impurities are removed when the additive is removed by filteration after the above heat treatment.

For example, air sampling is done using reusable cassettes with a filter, or disposable cassettes with filters, where after passing a predetermined amount of air, the filter from the reusable cassette or the entire cassette from the later are put in the acid solution and heated to an elevated temperature to extract beryllium into the solution. The advantage of the latter is that any beryllium sticking to the cassette walls is also considered. For surface analysis wipes are used to wipe a certain area of the surface and then these are treated in an acid solution to extract beryllium.

To check how the air sampling medium (cassette or the air filter) influences the background fluorescence the following types of media were analyzed: disposable cassettes with air filters from Air Sampling Devices called Solusert™, 37 mm cassette insert, Cat CLCL-C3750, Lot 13G-030E13 (Milford, N.H.) and 0.8 μm MCE filters from SKC. were analyzed for their background fluorescence.

These filters or disposable Solusert™ cassettes were added to vials containing 5 ml of 1% ABF solution in water and extracted for one hour at 85° C. after capping the vials. After cooling, the background fluorescence of these was measured along with virgin 1% ABF solution (blank). In addition this solution was also added to a fluorescent dye solution (dye Solution "B" as described earlier, 3× dilution) and the fluorescent signal was measured. An aliquot of these solutions were then taken and mixed with cleaned charcoal (available as BeFinder CB-1 from Berylliant Inc in Tucson, Ariz.) in a concentration of 1 mg of charcoal/1 ml of the above solution and heated at 85° C. for one hour in capped vials. After this was cooled to room temperature, these solutions were filtered using 0.2 μm Acrodisc GHP Hydrophilic Polypropylene syringe filters to remove the charcoal, and then these solutions were measured for their fluorescence with and without adding the dye solution. The dye solution used was Solution "B" at 3× dilution (i.e., one part was the acidic solution with 2 parts of the dye solution by volume). The data is shown in Table 15. Since at 3× dilution the amount of sample solution is very high relative to the dye solution, background fluorescence can contribute significantly to the signal and degrade the detection limit performance. As seen in the table this degradation is expected to be higher when using Solusert™ cassettes as compared to the MCE filters, unless the fluorescent impurities are removed.

TABLE 15

Fluorescence signal (intensity arbitrary units) from various blank samples (no added beryllium) with and without the dye solution and also before and after the charcoal treatment.

| | Type of solution | | | |
|---|---|---|---|---|
| | Sample solution not treated with Charcoal | | Sample solution treated with Charcoal | |
| | Without Dye Solution | With Dye Solution "B", Dilution ratio 3X | Without Dye Solution | With Dye Solution "B", Dilution ratio 3X |
| 1% ABF | 30 | 110 | 30 | 110 |
| MCE filter, after extracting with 1% ABF | 150 | 150 | 30 | 120 |
| Solusert ™ cassette, after extracting with 1% ABF | 300 | 280 | 65 | 125 |

Example 10: Change in pH of a Buffered Dye Solution with Addition of Sodium Hydroxide A standard buffered dye solution (using lysine as the buffer) was made as in Example 1 (Solution "A") and its pH was measured to be 12.85 following the procedure described in the said Example. The amount of sodium hydroxide (or base without buffer) was about 8.27% in the total dye solution. This is the same solution used in Example 1 and called Solution "A".

10 g aliquots were taken of the above solution and to one 0.0413 g of 2.5 N NaOH solution was added and to the other 0.0826 g of 2.5 N NaOH was added. These additions corresponded to increasing the base or the sodium hydroxide content by 5% in the first case and by 10% in the second case. The pH of the buffered solution with 5% excess base was 12.88 and for 10% excess base it was 12.91. The pH change was linear with change in the amount of base within the range evaluated above. Interpolation in this range showed that with 8% extra addition of the base, the pH would have been 12.9.

This invention teaches a method to determine the presence of beryllium or a beryllium compound in a sample by measuring optical fluorescence. Beryllium from a sample is extracted in an acidic aqueous liquid medium (unless beryllium is already in an aqueous medium) and mixed with a solution containing a fluorescent dye which binds with beryllium and results in a fluorescent signal when excited using appropriate optical radiation. The intensity of the fluorescent signal correlates with the beryllium content in the mixed solution which is used to determine the beryllium content of the sample.

A solution comprising beryllium from a sample is mixed with a highly alkaline solution containing fluorescent dye which has a pH of 12.9 or higher, preferably 13 or higher and most preferably at or higher than 13.1. Alternatively, the highly alkaline solution has at least 8% more base as compared to standard buffered solutions, and preferably at least 20%. The amount of beryllium in this mixture is measured by the intensity of fluorescence which results from the binding of the dye with beryllium. In one embodiment the dye solution has no pH buffer. Beryllium from a solid sample is extracted typically by treating the sample in a liquid medium, and typically in an acidic aqueous solution in which beryllium from the sample is extracted or dissolved to obtain beryllium sample in a solution. Some examples of solid samples are soils, rocks, sediments, fly ash, metals, ores, surface wipes, air filters, body tissues, bones, plants, seeds, etc. In some cases the beryllium sample may be naturally in a solution, such as in water and a body fluid e.g., blood, fluid from a tumor, urine, extracted fluid from a plant, fruit and vegetable, etc.). Examples of acidic medium are solutions of ammonium bifluoride (ABF), HF, HCl, HNO3, H2SO4, HClO4, and mixtures of these. The extraction in the liquid medium may be done at any temperature, but a preferred temperature is an elevated temperature generally above 60° C. and more preferably at or above 80° C. For economical reasons, i.e., it is desirable to extract beryllium from large number of samples without using expensive hardware and pressure vessels, this extraction is preferably carried out under ambient pressure at a temperature at or below the boiling point of the acidic medium in capped plastic containers. These plastic containers may be inexpensive and be disposable. Thus a highly preferred range of temperature for extracting beryllium is about 60 to 100° C. and a more preferred range between 80 to 100° C. In a preferred embodiment the alkalinity of the highly alkaline fluorescent dye solution may also be measured in another way. The highly alkaline dye solution (i.e., the solution comprising the fluorescent indicator) when mixed with an acidic solution comprising 8 wt % of ABF in a ratio of 19:1 by volume (20× dilution ratio) the pH of the mixture should still stay above 11, preferably above 12.

In another embodiment, the highly alkaline fluorescent dye solution has a pH of at least 12.9, preferably above 13, more preferably above 13.1. The highly alkaline solution preferably does not contain pH buffer. As noted above beryllium is extracted into a liquid medium from a sample (unless beryllium is present in the liquid to be analyzed) and then mixed with the dye solution to measure fluorescence in order to determine beryllium content in the sample.

In another embodiment, the method includes measuring beryllium by mixing liquid comprising beryllium with a highly alkaline dye solution, where the pH of the mixture is at least 11, preferably at least 12.

In yet another embodiment, the use of highly alkaline solutions allows one to mix these with sample solutions in a dilution ratio of 4× or lower. This means that the volumetric ratio of beryllium containing solution to the dye containing highly alkaline solution is 1:3 or higher. Lower dilution ratio allows one to measure lower amounts of beryllium (increased detection limits). The liquid comprising beryllium may be obtained by extracting beryllium from a solid sample into a liquid medium. The pH of the dye solution itself may be higher than 12.9 and may not contain any pH buffer.

In summary, some of the important advantages for highly alkaline solutions are: (a) easier and more consistent preparation of dye solutions, (b) higher acidity solutions can be used to more rapidly extract beryllium from more refractory materials, (c) lower dilution ratios could be used for enhanced beryllium sensitivity, (d) the possibility of interference with other metals is reduced, and (e) a wider range of acidic solutions can be used to extract beryllium from metallic samples such as aluminum and its alloys.

It will be understood that various modifications may be made to the embodiments disclosed herein. Hence the above description should not be construed as limiting, but merely as exemplifications of preferred embodiments. Those skilled in the art will envision other modifications that come within the scope and spirit of the claims appended hereto.

What is claimed is:
1. A method of determining a presence or an amount of beryllium or beryllium compound in a sample comprising:
   (a) extracting the beryllium or the beryllium compound from the sample into a liquid medium unless the sample itself is a liquid medium;
   (b) combining the liquid medium comprising the beryllium or the beryllium compound with a second solution creating a mixture, wherein the second solution contains a fluorescent indicator and a pH of the second solution is greater than 12.9 and;
   (c) measuring optical fluorescence of the mixture, and correlating the optical fluorescence of the mixture with the presence or the amount of the beryllium or the beryllium compound within said mixture wherein the second solution with the fluorescent indicator contains no buffer.

2. A method as in claim 1, wherein the liquid medium further comprises an 8% or higher concentration by weight of ammonium bifluoride (ABF) solution in water, and mixing the liquid medium with the second solution in a volumetric ratio of 1:19 results in a pH value of at least 11.

3. A method as in claim 1, wherein the sample is obtained from at least one of a water sample, body fluid, soils, rocks, sediments, fly ash, metals, ores, surface wipes, air filters, body tissues, bones, plants or seeds.

4. A method as in claim 3, wherein the liquid medium comprising the beryllium or the beryllium compound and the second solution are combined in a dilution ratio of 4× or lower.

5. A method as in claim 3 where the extraction of the beryllium or the beryllium compound into the liquid medium is carried out in a temperature range of about 60 to 100° C.

6. A method as in claim 3, wherein the liquid medium comprising the beryllium or the beryllium compound further comprises 8% or higher concentration by weight of ammonium bifluoride (ABF) solution in water.

7. A method as in claim 1, wherein the liquid medium and the second solution are combined in a volumetric ratio of 1:3 or higher.

8. A method of determining a presence or an amount of beryllium or beryllium compound in a sample comprising;
   (a) extracting the beryllium or the beryllium compound from the sample into a liquid medium unless the sample itself is a liquid medium;
   (b) combining the liquid medium containing the beryllium or the beryllium compound with a solution comprising at least one fluorescent indicator in a volumetric ratio of 1:3 or higher creating a mixture, where a 1 pH of the resulting mixture is at or greater than 12; and
   (c) measuring optical fluorescence of the mixture, and correlating the optical fluorescence of the mixture with the presence or the amount of the beryllium or the beryllium compound within the mixture wherein the presence or the amount of the beryllium within the sample is detectable at a limit lower than 0.001 μg.

9. A method as in claim 8, wherein the solution comprising the at least one fluorescent indicator has a pH greater than 12.9.

10. A method as in claim 8 where the extraction of the beryllium or the beryllium compound into the liquid medium is carried out in a temperature range of about 60 to 100° C.

11. A method of determining a presence or an amount of beryllium or beryllium compound in a sample comprising;
   (a) extracting the beryllium or the beryllium compound from the sample into a liquid medium unless the sample itself is a liquid medium, wherein the liquid medium further comprises an 8% or higher concentration by weight ammonium bifluoride (ABF) solution in water;

(b) combining the liquid medium containing the beryllium or the beryllium compound with a solution comprising at least one fluorescent indicator in a volumetric ratio of about 1:19 or higher, creating a resulting mixture, where a pH of the resulting mixture is at or greater than 12; and (c) measuring optical fluorescence of the resulting mixture, and correlating the optical fluorescence of the resulting mixture with the presence or the amount of the beryllium or the beryllium compound within the resulting mixture wherein the solution comprising at least one fluorescent indicator contains no buffer.

* * * * *